United States Patent [19]

Fukui et al.

[11] Patent Number: 4,662,758
[45] Date of Patent: May 5, 1987

[54] OPTICAL DETECTOR ASSEMBLY

[75] Inventors: Tomonori Fukui; Yukiyasu Ueno, both of Kariya, Japan

[73] Assignee: Nippondenso Co., Ltd., Kariya, Japan

[21] Appl. No.: 611,156

[22] Filed: May 17, 1984

[30] Foreign Application Priority Data

| May 18, 1983 | [JP] | Japan | 58-87242 |
| Dec. 22, 1983 | [JP] | Japan | 58-242869 |
| Dec. 22, 1983 | [JP] | Japan | 58-242868 |
| Dec. 22, 1983 | [JP] | Japan | 58-242866 |
| Apr. 6, 1984 | [JP] | Japan | 59-69742 |

[51] Int. Cl.$^4$ ............................................. G01N 21/17
[52] U.S. Cl. ...................................... 356/439; 250/573; 165/42
[58] Field of Search ............................ 356/432–442, 356/335–339, 37; 250/573–575; 350/582–584; 364/424; 165/42

[56] References Cited

U.S. PATENT DOCUMENTS

| 3,170,068 | 2/1965 | Petriw et al. | 356/437 X |
| 3,524,707 | 8/1970 | Hansen et al. | 356/439 X |
| 4,113,386 | 9/1978 | Lepper | 250/574 X |
| 4,238,194 | 12/1980 | Dunham | 356/37 X |
| 4,259,722 | 3/1981 | Iwata et al. | 364/424 |
| 4,437,391 | 3/1984 | Eguchi et al. | 364/424 X |

FOREIGN PATENT DOCUMENTS 679904 8/1979 U.S.S.R. ............................... 356/37

Primary Examiner—R. A. Rosenberger
Attorney, Agent, or Firm—Cushman, Darby & Cushman

[57] ABSTRACT

An optical detector assembly comprises a casing formed therein with a through bore having front and rear openings and a pair of opposite cavities located at both sides of the through bore, an air duct member disposed within the through bore to permit the flow of air passing therethrough, the duct member being formed at its peripheral wall with a pair of radial holes opening toward the cavities respectively, a light emission element arranged within one of the cavities to emit a luminous ray and pass it through the radial holes of the duct member toward the other cavity, a light receiving element arranged within the other cavity to receive the luminous ray emitted from the light emission element and passed through the radial holes, and an air induction assembly coupled over the front opening of the through bore for preventing entry of alien particles such as dirt, water, snow and the like into the duct member.

5 Claims, 19 Drawing Figures

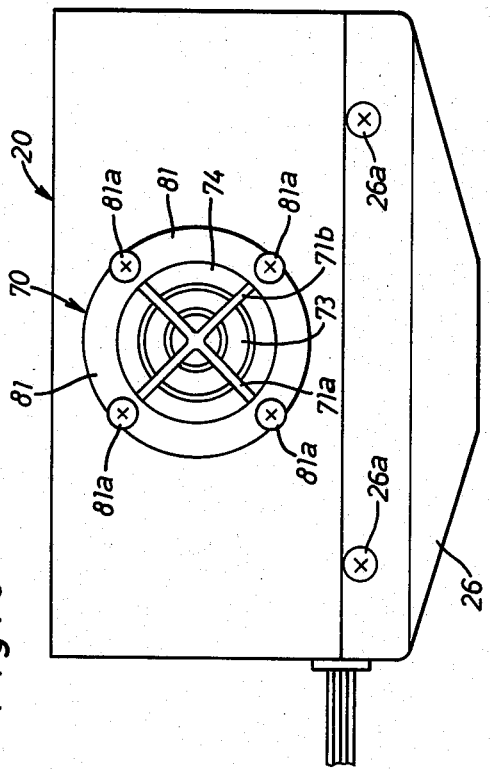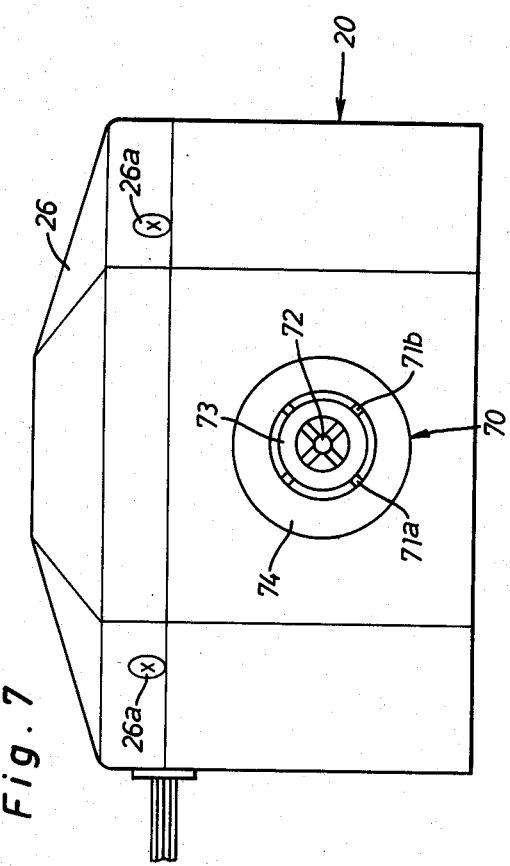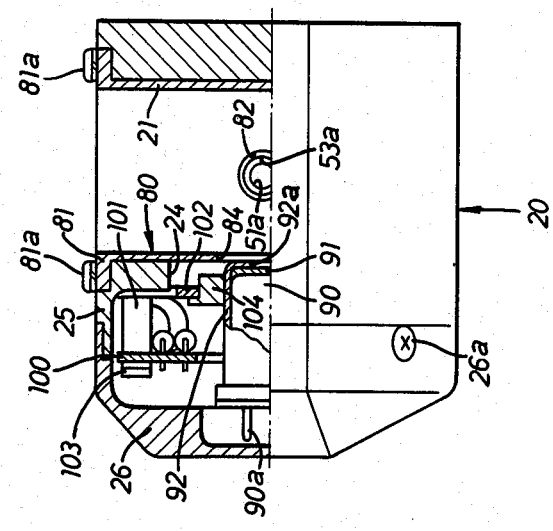

OPTICAL DETECTOR ASSEMBLY

BACKGROUND OF THE INVENTION

The present invention relates to an optical detector assembly, and more particularly to an optical detector assembly for detecting concentration of dust, smoke or the like contained in the flow of air passing therethrough.

In an optical detector assembly of this kind, optical elements such as a light emission element, a light receiving element and lens will suffer in their functions from dust adhered thereto. Particularly, in adaptation of the optical detector assembly to an automobile, there will occur an error in detection due to presence of alien particles such as dirt, water, snow and the like in the flow of dust to be detected by the optical elements. It is also apparent that if such alien particles adhere to the optical elements, the function of the detector assembly will suffer severely. Furthermore, there will occur an error in detection due to presence of an external disturbance light entering into the light receiving element of the detector assembly.

SUMMARY OF THE INVENTION

It is, therefore, a primary object of the present invention to provide an optical detector assembly the optical elements of which are protected from dust and alien particles to reliably detect concentration of dust in the flow of air passing therethrough.

A secondary object of the present invention is to provide an optical detector assembly, having the above-mentioned characteristics, capable of detecting concentration of dust in the flow of air without an error caused by an external disturbance light entering into the detector assembly.

According to the present invention, the primary object is accomplished by provision of an optical detector assembly which comprises a casing formed therein with a through bore having front, and rear openings and a pair of lateral cavities located at both sides of the through bore, an air duct member disposed within the through bore to permit the flow of air passing therethrough, the air duct member being formed at its peripheral wall with a pair of radial holes opening toward the cavities respectively, a light emission element arranged within one of the cavities to emit a luminous ray and pass it through the radial holes of the duct member toward the other cavity, a light receiving element arranged within the other cavity to receive the luminous ray emitted from the light emission element through the radial holes of the air duct member, and an air induction assembly coupled over the front opening of the through bore and including means for preventing entry of alien particles such as dirt, water, snow and the like into the air duct member to pass only dust and gases contained in the flow of air toward the interior of the air duct member.

In the optical detector assembly, preferably, each of the cavities is provided therein with a plurality of laterally spaced partition plates each of which is formed with a small hole in alignment with the radial holes of the air duct member, the small holes in the partition plates being arranged on a common axis to permit the luminous ray passing therethrough from the light emission element to the light receiving element, and the small holes in the partition plates respectively adjacent to the light emission element and the light receiving element are determined to be smaller than those in the partition plates respectively adjacent the radial holes of the air duct member.

The secondary object of the present invention is accomplished by provision of an optical detector assembly having the above construction, in which the light emission element includes a luminous semiconductor and the light receiving element includes a photo-semiconductor, and in which the detector assembly further comprises an electric circuit including oscillation means for generating a series of oscillation signals, a transistor having a base connected to an output terminal of the oscillation means, a collector connected to an electric power source, and an emitter connected to the luminous semiconductor, and a resistor interposed between the collector and emitter of the transistor to constantly activate the luminous semiconductor at a predetermined level.

In a preferred embodiment of the present invention, the air induction assembly of the optical detector assembly comprises a cover member coupled over the front opening of the through bore and having an opening smaller than the front opening of the through bore, and a partition member located within the cover member and having a front face for receiving alien particles entering into the opening of the cover member, the parition member being arranged to form an annular passage opening toward the center of the air duct member.

BRIEF DESCRIPTION OF THE DRAWINGS

Additional objects and advantages of the present invention will be more readily apparent from the following detailed description of preferred embodiments thereof when taken together with the accompanying drawings, in which:

FIG. 5 is a partly broken side view of the detector assembly;

FIG. 6 is a rear view of the detector assembly;

FIG. 7 is a front view of the detector assembly;

DETAILED DESCRIPTION OF THE PREFERRED EMBODIMENTS

Figure 1:
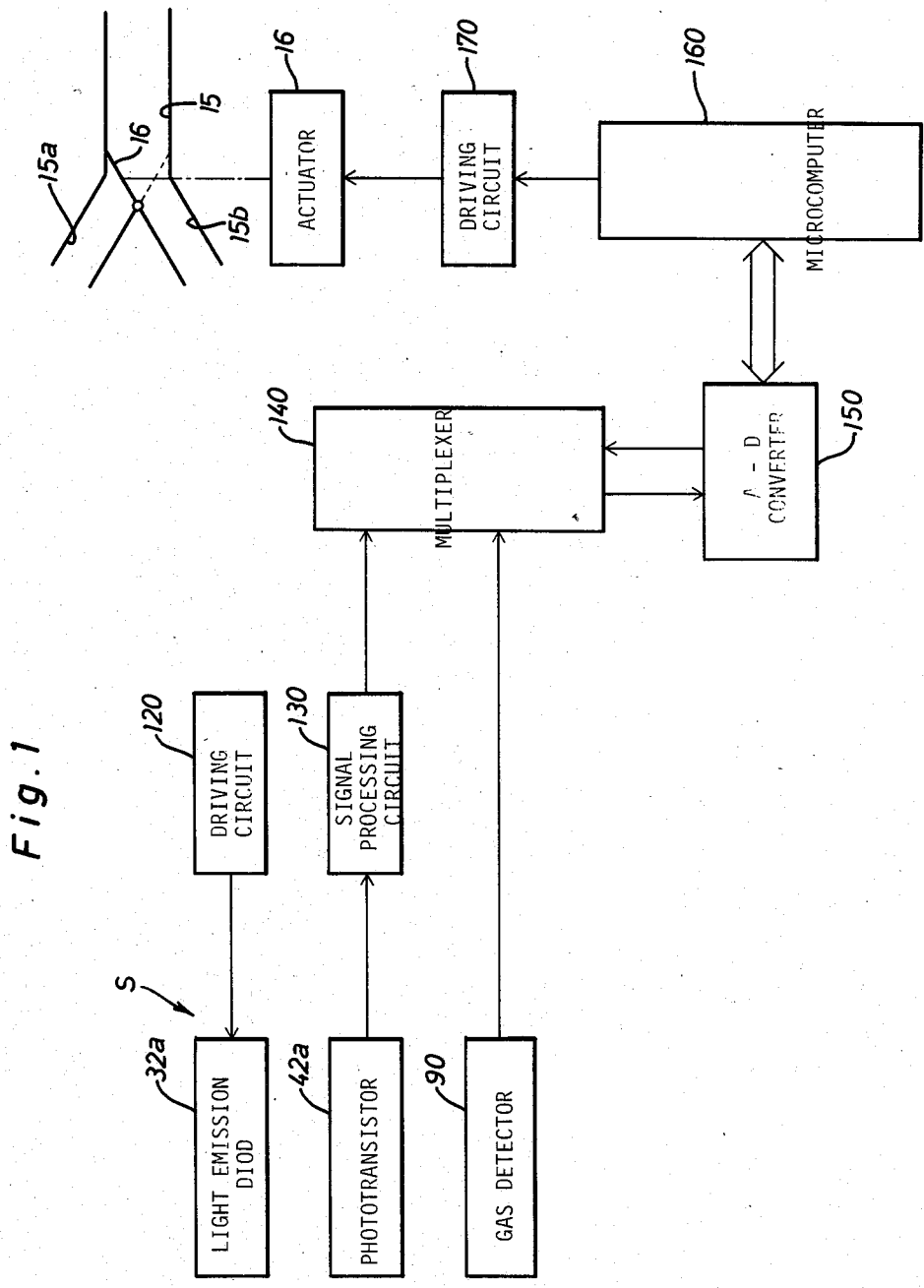
FIG. 1 is a schematic block diagram of an electric control apparatus for an automobile air conditioner in combination with an optical dust detector assembly in accordance with the present invention.
Figure 2:
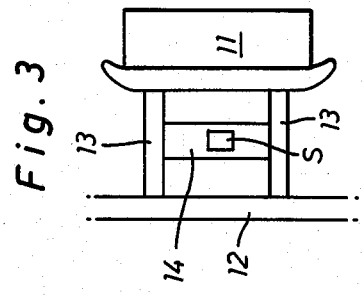
FIGS. 2 and 3 illustrate arrangements of the detector assembly on a vehicle body structure.
Figure 3:
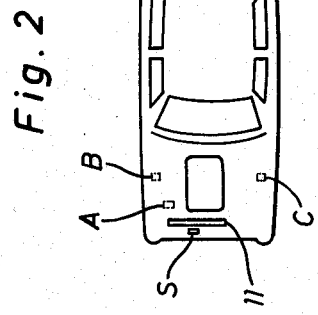
Figure 10:
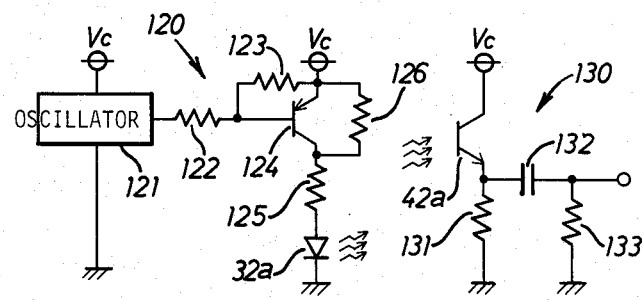
FIG. 10 illustrates a driving circuit for a light emission diode and a signal processing circuit for a phototransistor.

With reference to the drawings, FIG. 1 schematically illustrates an optical dust detector assembly S of the light transmission type in accordance with the present invention which is adapted to an electric control apparatus for an automobile air conditioner. As is illustrated in FIGS. 2 and 3, the optical dust detector assembly S is fixedly mounted on a lateral plate 14 the opposite ends of which are fixed to a pair of parallel chassis arms 13, 13 bridged between a radiator in front of a vehicle engine 10 and a front bumper 12 of the vehicle. As is illustrated in FIGS. 4 to 7, the optical dust detector assembly S includes a casing 20 which is arranged on the lateral plate 14 in a fore-and-aft direction of the vehicle. The casing 20 is provided therein with a fore-and-aft through bore 21 and a pair of lateral stepped bores 22, 23 each having a rectangular cross-section. The lateral stepped bores 22 and 23 are arranged symmetrically with respect to the through bore 21. In the interior of casing 20, a light emission assembly 30 is arranged within a small diameter portion 22a of stepped bore 22, while a light receiving assembly 40 is arranged within a small diameter portion 23a of stepped bore 23. The light emission assembly 30 includes an annular support member 31 of elastic synthetic resin and a light emission element 32. The annular support member 31 is formed at its outer periphery with an annular projection 31a which is fixedly coupled with an annular groove in the small diameter portion 22a of stepped bore 22 to resiliently support the light emission element 32 in place coaxially with the stepped bore 22. The light emission element 32 is directed to an opening of stepped bore 22 in such a manner that the light emission axis of element 32 coincides with the central axis of stepped bore 22. As is illustrated in FIG. 10, the light emission element 32 is provided therein with a light emission diode 32a from which a luminous ray is intermittently emitted in the form of pulses, as will be described later.

The light receiving assembly 40 includes an annular support member 41 of elastic synthetic resin and a light receiving element 42. The annular support member 41 is formed at its outer periphery with an annular projection 41a which is fixedly coupled with an annular groove in the small diameter portion 23a of stepped bore 23 to resiliently support the light receiving element 42 in place coaxially with the stepped bore 23. The light receiving element 42 is directed to an opening of stepped bore 23 to receive at its center the luminous ray from light emission element 32. As is illustrated in FIG. 10, the light receiving element 42 is provided therein with a phototransistor 42a which is energized in response to the intermittent luminous rays from light emission diode 32a to generate a series of intermittent pulses.

A large diameter portion 22b of stepped bore 22 is formed in its inner wall with annular grooves 22c, 22d, 22e and 22f which are laterally spaced in a predetermined distance and positioned perpendicularly to the central axis of stepped bore 22. Four rectangular partition plates 50, 51, 52 and 53 are fixedly coupled at their outer peripheries with the annular grooves 22c, 22d, 22e and 22f of the large diameter bore portion 22b. The partition plates 50, 51, 52 and 53 are formed at their central portions with small holes 50a, 51a, 52a and 53a respectively. Both the small holes 50a and 51a in plates 50 and 51 are the same in their opening areas, and both the small holes 52a and 53a in plates 52 and 53 are the same in their opening areas and larger than those in plates 50, 51. For instance, each diameter of the small holes 50a, 51a is determined to be 4.5 mm, and each diameter of the small holes 52a, 53a is determined to be 6.5 mm.

A large diameter portion 23b of stepped bore 23 is formed in its inner wall with annular grooves 23c, 23d, 23e and 23f which are laterally spaced in a predetermined distance and positioned perpendicularly to the central axis of stepped bore 23. Four rectangular partition plates 60, 61, 62 and 63 are fixedly coupled at their outer peripheries with the annular grooves 23c, 23d, 23e and 23f. The partition plates 60, 61, 62 and 63 are formed at their central portions with small holes 60a, 61a, 62a and 63a. Each opening area of the small holes 60a, 61a is the same as that of the small holes 50a, 51a in partition plates 50, 51, and each opening area of the small holes 62a, 63a is the same as that of the small holes 52a, 53a.

Figure 4:
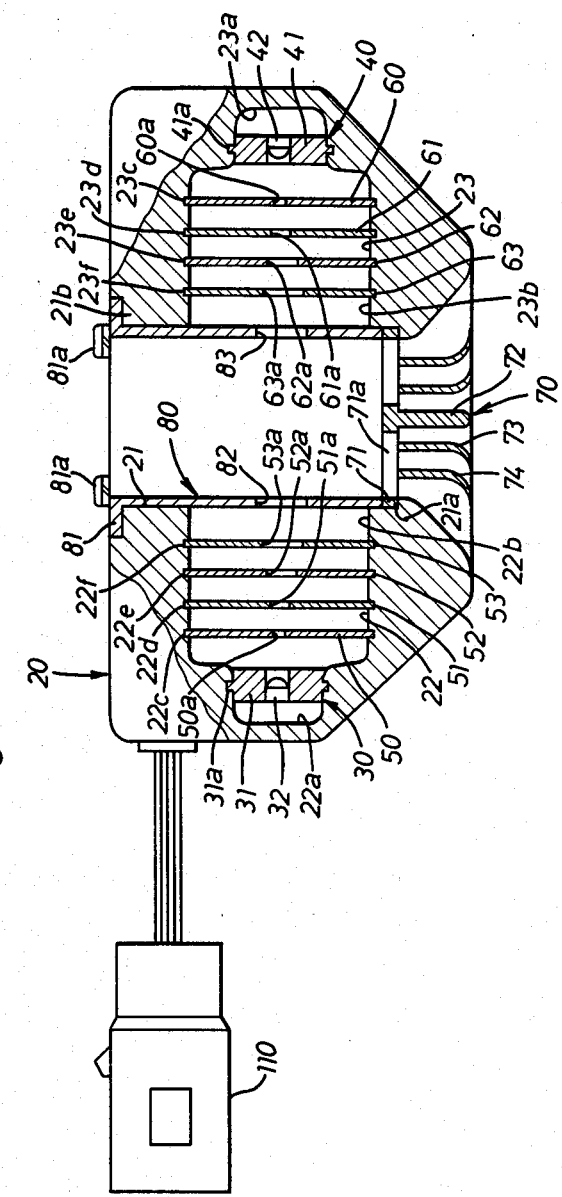
FIG. 4 is a partly broken cross-sectional view of the detector assembly.
Figure 8:
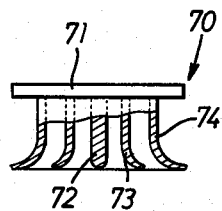
FIG. 8 is a part sectional view of an air induction assembly for the detector assembly.
Figure 9:
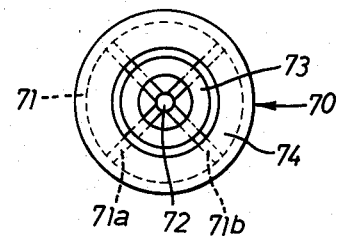
FIG. 9 is a front view of the air induction assembly.

As is illustrated in FIG. 4, an air induction assembly 70 and an air duct member 80 are disposed within the through bore 21 in casing 20. As can be well seen in FIGS. 4, 6, 7, 8 and 9, the air induction assembly 70 has a ring member 71 of hard synthetic resin fixedly coupled with a front annular stepped portion 21a of through bore 21, two crossed support arms 71a, 71b integral with the inner periphery of ring member 71, and a short rod 72 extending outwardly from the center of support arms 71a, 71b and arranged coaxially with the through bore 21. The front end of rod 72 is formed in a spherical shape to effect smooth flow of air with dust into the cylindrical air duct member 80. The air induction assembly 70 further includes a pair of radially spaced cylindrical members 73, 74 which extend outwardly from support arms 71, 71b and surround the rod 72. The cylindrical members 73, 74 are curved radially outwardly at their front ends to prevent entry of alien particles such as dirt, water, snow and the like into the cylindrical air duct member 80. Additionally, respective radial spaces between cylindrical members 73 and 74, between inner cylindrial member 73 and rod 72, and between outer cylindrical member 74 and ring member 71 are determined to prevent entry of the alien particles into the cylindrical air duct member 80 so as to permit only the flow of air into the cylindrial air duct member 80.

The air duct member 80 is coupled within the through bore 21 of casing 20 and fastened at its annular flange 81 by screws 81a—81a threaded into the casing. Thus, the air duct member 80 is positioned in place by engagement with an annular stepped portion 21b of through bore 21 to fasten the ring member 71 of air induction assembly 70 in place. (see FIGS. 4, 5 and 6) The air duct member 80 is formed in its peripheral wall with a pair of radial holes 82 and 83 which are alinged with the central axes of respective stepped bores 22 and 23. Each opening area of radial holes 82, 83 is the same and is extremely smaller than the cross-sectional area of the air duct member 80. The opening areas of radial holes 82, 83 are larger than those of small holes 53a, 63a in partitionplates 53, 63. As can be well seen in FIG. 5, the air duct member 80 is further formed in its peripheral wall with a radial hole 84 which is located perpendicularly to the central axes of respective stepped bores 22 and 23. The casing 20 is further provided therein with a radial opening 24 in open communication with the radial hole 84 of air duct member 80 and with a cavity 25 in a surrounding relationship with the radial opening 24 and being closed by a cover member 26 fastened in place by screws 26a, 26a threaded into the casing 20.

Assembled within the cavity 25 are a gas detector 90 and a printed base plate 100. The gas detector 90 is contained within a cup-shaped protector case 92 which is fixed to the inner wall of cover member 26 and extends through the radial opening 24 toward the radial hole 84 of air duct member 80. The protector case 92 is formed at its bottom portion with apertures 92a and contains a porous membrane 91 located at the bottom of gas detector 90. Thus, the gas detector 90 is exposed to gases flowing through the air duct member 80 and entering into the case 92 through opening 84, bottom apertures 92a and porous membrane 91. In this embodiment, the gas detector 90 is of the solid thermal conduction type which detects concentration of the gases applied thereto to generate an electric signal indicative of the detected concentration from its output terminal 90a. The printed base plate 100 is fixed in place by screws 103 threaded into the casing 20 through a spacer 101 and an annular base plate 102. The printed base plate 100 includes electric circuits printed thereon through which the light emission element 32, the light receiving element 42 and the gas detector 90 are connected to a connector 110. (see FIG. 4) In FIG. 5, the reference numeral 104 designates a grommet for protection of the printed base plate 100.

Subsequently, a driving circuit 120 for light emission diode 32a and a signal processing circuit 130 for phototransistor 42a will be described in detail with reference to FIGS. 1 and 10. The driving circuit 120 includes an oscillator 121 and a transistor 124. The oscillator 121 is applied with a supply voltage Vc from a DC voltage source to generate a series of oscillation pulses. The transistor 124 has a base connected to an output terminal of oscillator 121 through a resistor 122, an emitter grounded through a resistor 125 and the light emission diode 32a, and a collector connected to its base through a resistor 123. When applied at its collector with the supply voltage Vc from the DC voltage source, the transistor 124 is intermittently energized in response to the oscillation pulses from oscillator 121 under bias functions of the resistors 122 and 123, and in turn, the light emission diode 32a is intermittently applied through transistor 125 with an electric current from the emitter of transistor 124 the value of which is determined by an internal resistance value of transistor 124. The driving circuit 120 is characterized by provision of a resistor 126 which is interposed between the emitter and collector of transistor 124. When applied with the supply voltage Vc from the DC voltage source, the resistor 126 applies an electric current to the light emission diode 32a through resistor 125 irrespectively of energization of the transistor 124. The value of the electric current to light emission diode 32a is determined by a resistance value of resistor 126.

With the above arrangement, the light emission diode 32a is supplied with the electric current through resistors 125, 126 during deenergization of the transistor 124 to emit a luminous ray at a standard level a. When the transistor 124 is energized, the light emission diode 32a is further supplied with the electric current from the emitter of transistor 124 through resistor 125 to emit a luminous ray at a high level defined by addition of a predetermined level and the standard level $\alpha$. Thus, the light emission diode 32a emits a series of intermittent luminous rays in the form of pulses, as is illustrated by a character a in FIG. 11. For the above purpose, the resistance value of resistor 126 is determined to constantly activate the phototransistor 42a.

The signal processing circuit 130 includes a resistor 131 which is grounded at one end thereof and connected at the other end thereof to an emitter of phototransistor 42a. This means that when applied with the supply voltage Vc from the DC voltage source, the phototransistor 42a produces a series of intermittent pulses in response to the intermittent luminous rays from light emission diode 32a. The emitter of phototransistor 42a is further connected to one end of a condensor 132 the other end of which is grounded through a resistor 133. The condensor 132 is provided to eliminate a direct current part from the intermittent pulses so as to successively produce the remaining part of them as a series of detected pulses. In such an arrangement as described above, each amplitude width of the detected pulses from condensor 132 will decrease in proportion to decrease of the intensity of luminous ray applied to phototransistor 42a from light emission diode 32a, and distortion in wave form of the detected pulses will increase in accordance with increase of the intensity of luminous ray applied to phototransistor 42a.

Figure 11:
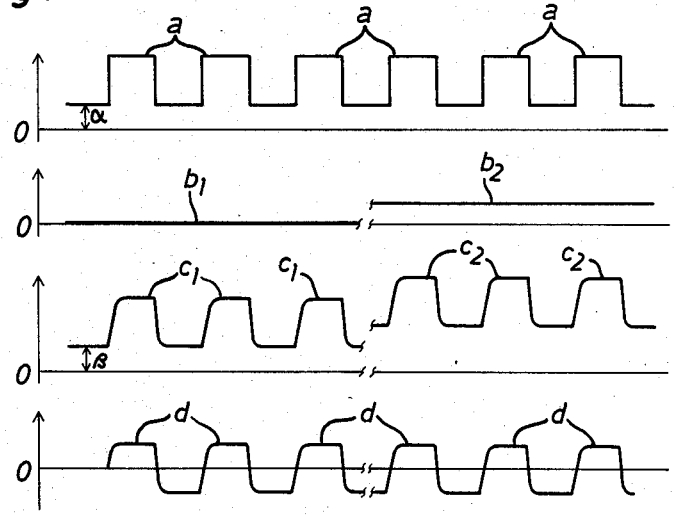
FIG. 11 illustrates wave forms of output signals from the signal processing circuit in relation to luminous rays emitted from the light emission diode.

Assuming that the optical dust detector assembly S is being activated when the vehicle is running, the transistor 124 of driving circuit 120 is intermittently energized in response to the oscillation pulses from oscillator 121 to intermittently apply an electric current defined by its internal resistance value to the light emission diode 32a through resistor 125, while the resistor 126 constantly applies an electric current defined by its resistance value to the light emission diode 32a through resistor 126. As a result, the light emission diode 32a is being energized by the electric current flowing through resistor 126 during deenergization of transistor 124. When the transistor 124 is energized, the light emission diode 32a is energized by both the electric currents respectively flowing through transistor 124 and resistor 126 to emit intermittent luminous rays in the form of pulses above the standard luminous level $\alpha$, as is illustrated by the character a in FIG. 11. The intermittent luminous rays from light emission diode 32a pass through the small holes 50a–53a in partition plates 50–53 along the light emission axis of element 32 and enter into the air duct member 80 across its radial hole 82. Thus, the intermittent luminous rays pass across the air flowing through the air duct member 80 and pass through the small holes 63a–60a in partition plates 63–60 to be received by the light receiving element 42. When received the intermittent luminous rays, the phototransistor 42a of light receiving element 42 is intermittently energized to produce a series of pulses $c_1$ as shown in FIG. 11. In this instance, the series of pulses $c_1$ are shifted by a level width $\beta$ corresponding with the standard luminous level $\alpha$ toward a positive side. Assuming that as shown by a character $b_1$, any external disturbance light does not exists, each leading wave form of the pulses $c_1$ is maintained without any distortion.

When the phototransistor 42a produces the series of light receiving pulses $c_1$ as described above, the condensor 132 of signal processing circuit 130 eliminates a direct current part from the pluses $c_1$ to produce a series of detected pulses d as shown in FIG. 11. In this instance, each of the detected pulses d appears approximately in the form of a rectangular shape without any distortion. Even if in such a condition the light receiving element 42 receives an external disturbance light entering across the small holes 63a–60a in partition plates 63–60, any distortion does not occur in each leading wave form of the detected pluses from condensor 132 because the series of pulses from phototransistor 42a are shifted by a level width corresponding with a value of the external disturbance light toward the positive side as shown by a character $c_2$ in FIG. 11.

If during activation of the optical dust detector S there occurs flow of dust, gases and the like passing through the air induction assembly 70 and entering into the air duct member 80, the quantity of light received by phototransistor 42a will decrease in accordance with the concentration of the flow of dust. As a result, the amplitude width of the detected pluses from condensor 132 will decrease, and some distortion will occur in wave form of the detected pulses irrespectively of presence of an external disturbance light. When the flow of dust and gases includes dirt, water or other dirty alien particles, the air induction assembly 70 prevents the air duct member 80 from entry of the dirt, water or dirty alien particles to permit only the flow of dust and gases therethrough into the air duct member 80. As a result, the quantity of light received by phototransistor 42a will decrease without any influence caused by the dirt, water or other dirty alien particles. Thus, decrease of the amplitude width of the detected pulses from condensor 132 and distortion in wave form of the pluses will correspond with concentration of dust in the flow.

Figure 12:
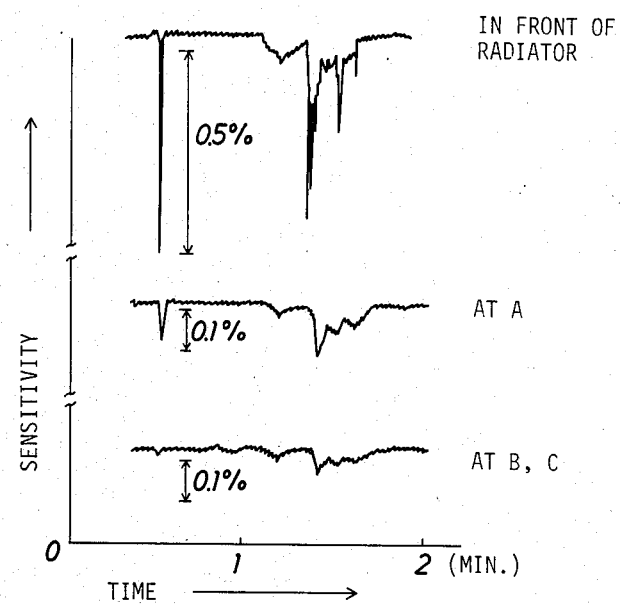
FIG. 12 is a graph illustrating sensitivity of the detector assembly in relation to arrangements of the same.

Since the optical dust detector assembly S is arranged in front of radiator 11 to directly receive the flow of outside air immediately before entering into the radiator, it is able to detect pollution of the outside air as accurately as possible in a good sensitivity. For the purpose of ascertaining a relationship between sensitivity of the optical dust detector assembly S and arrangement of the same, three optical dust detector assemblies A, B and C each having the same construction as that of the optical dust detector assembly S have been arranged as shown in FIG. 2. The first optical dust detector assembly A has been positioned behind the radiator 11 and adjacent the engine 10, the second optical dust detector assembly B has been positioned adjacent a right fender of the vehicle, and the third optical dust detector assembly C has been positioned adjacent a left fender of the vehicle. In FIG. 12, it is illustrated that sensitivity and responsibility of the optical dust detector assembly S in front of radiator 11 is better than those of the other three optical dust detector assemblies A, B and C.

Since the respective opening areas of radial holes 82, 83 of the air duct member 80, small axial holes 52a, 53a, 62a and 63a in partition plates 52, 53, 62 and 63, and small holes 50a, 51a, 60a and 61a in partition plates 50, 51, 60 and 61 are determined as described above, the flow of dust and gases entering into the small holes 53a, 63a does not occur. Even if a portion of dust and gases flows into the small hole 53a or 63a, such a flow of dust and gases will not reach the light emission element 32 or the light receiving element 42 because of the difference in diameter between small holes 51a and 52a or between small holes 61a and 62a. The flow of dust and gases entering into a space between the partition plates 51a and 52a or between the partition plates 61a and 62a becomes a diffusion flow and returns into the air duct member 80. For this reason, the light emission surface of element 32 and the light receiving surface of element 42 are protected from the dust flow to maintain normal function of the respective optical elements 32 and 42.

For the purpose of ascertaining a relationship between the optical function of dust detector S and dust-proof property of the same, the light emission element 32 has been replaced with a gas detector, and the number of partition plates in lateral stepped bore 22 of the casing 20, each opening area of small holes in the respective partition plates, and each space between the partition plates have been changed. In such arrangements, various experiments have been repeated by entering the flow of monoxide gas into the lateral stepped bore 22 to obtain the following results.

1. With regard to each opening area of the small holes in the partition plates:

In the case that first, second and third partition plates have been equidistantly arranged between the opening of lateral stepped bore 22 and the gas detector and that the small holes in the first, second and third partition plates have been determined to be $\phi 1$(mm), $\phi 2$(mm) and $\phi 3$(mm) in diameter respectively, the following data have been obtained. In these data, 17 in an amount of monoxide gas may correspond with 100 P.P.M..

TABLE 1

| Combination of diameters of the small holes | Amount of monoxide gas |
| --- | --- |
| $\phi 1 = 6.9$ mm<br>$\phi 2 = 5.6$ mm<br>$\phi 3 = 4.4$ mm | 30 |
| $\phi 1 = \phi 2 = 6.9$ mm<br>$\phi 3 = 4.4$ mm | 20 |
| $\phi 1 = 6.9$ mm<br>$\phi 2 = \phi 3 = 4.4$ mm | 20 |

From the above data, it has been observed that when each diameter of the small holes was determined as small as possible and the difference between $\phi 2$ and $\phi 3$ was determined to be larger than that between $\phi 1$ and $\phi 2$, the detected amount of monoxide gas was smallest.

2. With regard to the number of the partition plates:

In the case that the number of equidistantly spaced partition plates has been changed, the detected amount of monoxide gas has linearly decreased in accordance with increase of the number of the partition plates.

3. With regard to each space between the partition plates:

In the case that first through fifth partition plates have been provided respectively with a small hole of 4.4 mm in diameter and that each space between the adjacent partition plates has been changed, the following data have been obtained, where D12(mm) is a space between the first and second partition plates, D23(mm) is a space between the second and third partition plates, and D34(mm) is a space between the third and fourth partition plates.

TABLE 2

| Combination of spaces | Amount of monoxide gas |
| --- | --- |
| D12 = 14 mm, D23 = 7 mm<br>D34 = 14 mm | 17 |
| D12 = D23 = 14 mm,<br>D34 = 7 mm | 18 |
| D12 = D23 = D34 = 7 mm | 14 |
| D12 = D23 = D34 = 14 mm | 13 |

From the above data, it has been observed that when each space between the partition plates was determined as large as possible, the detected amount of monoxide gas was smallest.

When invisible gases flow into the air duct member 80 during activation of the optical dust detector assembly S, the gas detector 90 is exposed to the flow of gases through opening 84, bottom apertures 92a and porous membrane 91 to generate therefrom an electric signal indicative of concentration of the gases.

As is illustrated in FIG. 1, the automobile air conditioner includes an air duct 15 provided with a first inlet 15a for inducting outside air from the exterior into a passenger compartment (not shown) and with a second inlet 15b for recirculating inside air from the passenger compartment into the air duct, and a switch door 16 arranged within the air duct for effecting the induction of outside air in a first position and effecting the recirculation of inside air in a second position, and an actuator 16 arranged to switch over the switch door 16 from the first position to the second position in a first operative condition and to switch over the switch door 16 to the first position from the second position in a second operative condition. Furthermore, the electric control apparatus for the air conditioner comprises a multiplexer 140 connected to the signal processing circuit 130 and the gas detector 90, an A-D converter 150 connected to the multiplexer 140, a commercial available microcomputer 160 connected to A-D converter 150, and a driving circuit 170 connected to computer 160 for operating the actuator 16 of the air conditioner.

In the case that the optical dust detector assembly S is adapted to the above-described electric control apparatus for the air conditioner, the series of detected pulses from signal processing circuit 130 and the electric signal from gas detector 90 are selectively applied to A-D converter 150 by means of multiplexer 140 and converted into digital signals. When applied with the digital signals from A-D converter 150, the computer 160 executes calculations necessary for control of the switch door 16 based on values of the digital signals to generate a control signal therefrom, and subsequently the driving circuit 170 generates a drive signal in response to the control signal from computer 160. Thus, the actuator 16 is operated in response to the drive signal to switch over the switch door 16. In such operation of the electric control apparatus, the optical dust detector S will detect concentration of the dust flow immediately before entering into the radiator 11, and the signal processing circuit 130 will generate a series of detected pulses without any influence caused by an external disturbance light entering into the detector S. As a result, the switch door 16 is switched over in response to change of polluted condition of outside air to reliably block entry of polluted outside air into the passenger compartment.

Figure 13:
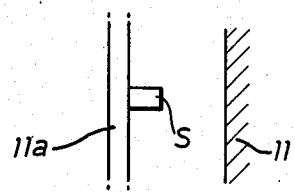
FIGS. 13, 14 and 15 illustrate another arrangements of the detector assembly on the vehicle body structure.
Figure 14:
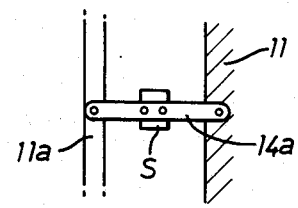
Figure 15:
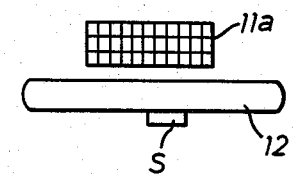

In adaptation to an automotive vehicle, the optical dust detector assembly S may be mounted on the back side of a front grille 11a of the vehicle as illustrated in FIG. 13. As shown in FIG. 14, the optical dust detector assembly S may be fixed to the bottom face of a plate 14a the opposite ends of which are secured to the upper face of front grille 11a and the upper face of radiator 11. Alternatively, the optical dust detector assembly S may be fixed to the bottom of a front dumper 12, as shown in FIG. 15. Although in the above embodiment, the optical dust detector assembly S is adapted to detect concentration of dust and gases contained in the air passing therethrough, it is adaptable as a smoke detector in a building.

Figure 16:
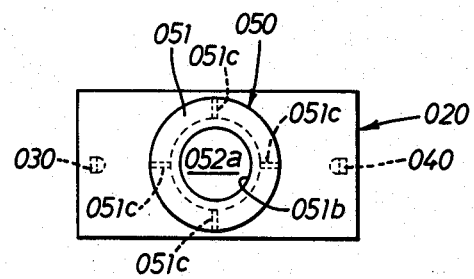
FIG. 16 is a front view of a modification of the detector assembly.
Figure 17:
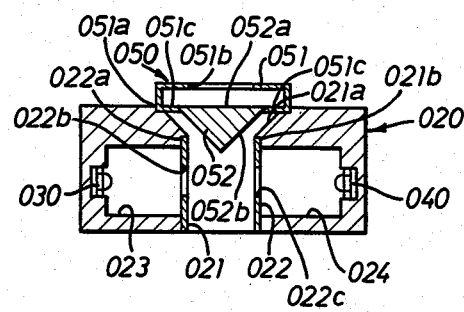
FIG. 17 is a sectional view of the detector assembly of FIG. 16.

In FIGS. 16 and 17, there is illustrated a modification of the optical dust detector assembly S which comprises a casing 020 formed at its central portion with a through bore 021 and formed therein with a pair of lateral cavities 023 and 024, a light emission element 030 arranged within the left cavity 023, a light receiving element 040 arranged within the right cavity 024, and an air induction assembly 050 for casing 020. The through bore 021 is formed at its front end with a tapered opening 021a. An air duct member 022 is coupled within the through bore 021 and positioned in place at its inner end by engagement with an annular stepped portion 021b of bore 021. The lateral cavities 023 and 024 are arranged symmetrically with respect to the axis of air duct member 022, and the air duct member 022 is provided at its peripheral wall with a pair of radial holes 022b and 022c which are aligned respectively with the light emission element 030 and the light receiving element 040. The light emission element 030 and the light receiving element 040 are substantially the same as those in the optical dust detector assembly S of FIG. 4.

The air induction assembly 050 is arranged to cover the tapered opening 021a of bore 021 and comprises an annular cover member 051 having a U-shaped cross-section, and a cone-shaped inner member 052 located at the center of cover member 051. The cover member 051 is secured at 051a to the casing 020 and is formed at its center with an opening 051b the diameter of which is smaller than that of the tapered opening 021a of casing 020. The cone-shaped inner member 052 is integrally secured at its outer periphery to the cover member 051 by means of four circumferentially spaced legs 051c. The inner member 052 has a front face 052a opposing to the opening 051b of cover member 051 and is associated at its peripheral surface 052b with the tapered opening 021a of casing 020 to form an annular passage opening toward the center of air duct member 022. The diameter of front face 052a is larger than that of the opening 051b of cover member 051 and smaller than that of the tapered opening 021a of casing 020.

Assuming that the optical dust detector assembly is being activated when the vehicle is running, intermittent luminous rays from the light emission element 030 pass through the radial holes 022b, 022c of air duct member 022 and are received by the light receiving element 040, while outside air flows into the air duct member 022 through the air induction assembly 050. If there occurs flow of dust, gases and the like passing through the air induction assembly 050 and entering into the air duct member 022, the quantity of light received by light receiving element 040 will decrease in accordance with concentration of the flow of dust. When the flow of dust and gases includes alien particles such as dirt, water, snow or the like, the inner member 052 of air induction assembly 050 receives the alien particles at its front face 052a to permit only the flow of dust and gases into the air duct member 22.

Figure 18:
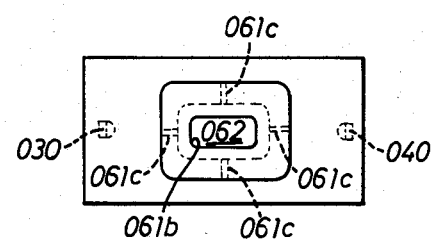
FIG. 18 is a front view of another modification of the detector assembly.
Figure 19:
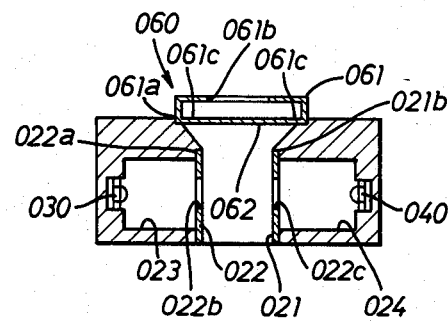
FIG. 19 is a sectional view of the detector assembly of FIG. 18.

In the actual practices of the present invention, the cone-shaped inner member 052 of air induction assembly 050 may be replaced with a circular plate secured at its outer periphery to the cover member 051 by means of circumferencially spaced support legs. Alternatively, the air induction assembly 050 may be replaced with an air induction assembly 060 as is illustrated in FIGS. 18 and 19. The air induction assembly 060 comprises a rectangular cover member 061 having a U-shaped cross-section and a rectangular plate 062. The rectangular cover member 061 is secured at 061a to the casing and has a rectangular opening 061b the diameter of which is smaller than a rectangular tapered opening of through bore 021 of the casing. The rectangular plate 062 is secured at its outer periphery to the cover member 061 by means of four circumferentially spaced support legs 061c to form an annular passage opening toward the center of air duct member 022. The surface area of plate 062 is larger than the opening area of cover member 061 and smaller than the area of the tapered opening of bore 021.

In the actual practices of the present invention, it is preferable that a thermal element such as a nichrome wire is mounted on the front surface of the inner member 052 of the air induction assembly 050 or the rectangular plate 062 of the air induction assembly 060 to be supplied with an electric current during activation of the optical dust detector assembly. In such a case, water or snow adhered to the inner member 052 or the plate 062 is heated by the thermal element to be vaporized.

Having now fully set forth both structure and operation of certain preferred embodiments of the concept underlying the present invention, various other embodiments as well as certain variations and modifications of the embodiments herein shown and described will obviously occur to those skilled in the art upon becoming familiar with said underlying concept. It is to be understood, therefore, that within the scope of the appended claims, the invention may be practiced otherwise than as specifically set forth herein.

What is claimed is:

1. An optical dust detector assembly adapted to an automobile air conditioner for detecting the concentration of dust contained in the flow of air entering into said air conditioner, said optical dust detector assembly comprising:
    a casing arranged in front of a radiator of the vehicle in a fore-and-aft direction, said casing being formed therein with a through bore having front and rear openings and a pair of lateral cavities located at both sides of said through bore, and the front opening of said casing being arranged to directly receive the flow of outside air immediately before entering into said radiator;
    a cylindrical air duct member disposed within said through bore to permit the flow of air passing therethrough, said air duct member being formed at its peripheral wall with a pair of radial holes opening toward said lateral cavities respectively;
    a light emission element arranged within one of said cavities to emit a luminous ray and pass it through the radial holes of said air duct member;
    a light receiving element arranged within the other cavity to receive the luminous ray from said light emission element through the radial holes of said air duct member;
    an air induction assembly coupled over the front opening of said through bore and including means for preventing entry of alien particles such as dirt, water, snow and the like into said air duct member to permit only dust and gases contained in the flow of air passing therethrough toward the interior of said air duct member; and
    a plurality of laterally spaced partition plates disposed in each of said lateral cavities, each of said plates being formed with a small hole in alignment with the radial holes of said air duct member, the small holes in said partition plates being arranged on a common axis to permit the luminous ray to pass therethrough from said light emission element to said light receiving element, the small holes in said partition plates respectively adjacent said light emission element and said light receiving elements being successively smaller in diameter than those in said partition plates respectively adjacent the radial holes of said air duct member thereby dust proofing said light receiving and light emission elements.

2. An optical dust detector assembly according to claim 1, wherein said partition plates are equidistantly spaced within each of said cavities.

3. An optical dust detector assembly according to claim 1, further comprising a gas detector assembly mounted within an additional cavity formed in said casing and opening toward the interior of said air duct member, said gas detector assembly being exposed to gases in the flow of air passing through said air duct member to detect concentration of the gases.

4. An optical dust detector assembly according to claim 1, wherein said light emission element includes a luminous semiconductor and said light receiving element includes a photo-semiconductor, and wherein said optical detector assembly further comprises an electric circuit including oscillation means for generating a series of oscillation signals; a transistor having a base connected to an output terminal of said oscillation means, a collector connected to an electric power source, and an emitter connected to said luminous semiconductor; and a resistor interposed between the collector and emitter of said transistor to constantly activate said luminous semiconductor at a predetermined level.

5. An optical dust detector assembly according to claim 1, wherein said air induction assembly comprises a cover member coupled over the front opening of said through bore and having an opening smaller than the front opening of said through bore, and a partition member located within said cover member and having a front face for receiving alien particles such as dirt, water, snow and the like entering into the opening of said cover member, said partition member being arranged to form an annular passage opening toward the center of said air duct member.

* * * * *